United States Patent [19]
Nakamura et al.

[11] Patent Number: 6,093,556
[45] Date of Patent: Jul. 25, 2000

[54] GENE RECOMBINANT WITH BIODEGRADABILITY FOR CHLORINATED ETHYLENE AND BIO-TREATMENT OF CHLORINATED ETHYLENE THEREWITH

[75] Inventors: Kanji Nakamura, Atsugi; Hiroaki Ishida, Isehara, both of Japan

[73] Assignee: Kurita Water Industries Ltd., Tokyo, Japan

[21] Appl. No.: 09/106,638

[22] Filed: Jun. 29, 1998

[30] Foreign Application Priority Data

Jun. 30, 1997 [JP] Japan .................................... 9-174996
Jun. 30, 1997 [JP] Japan .................................... 9-174997

[51] Int. Cl.[7] .............................. C12P 5/02; B09B 3/00; C07H 21/04
[52] U.S. Cl. ..................... 435/167; 435/262.5; 536/23.2
[58] Field of Search ......................... 536/23.2; 435/167, 435/262.5

[56] References Cited

PUBLICATIONS

Takeo et al. Molecular cloning and sequencing of the phenol hydroxylase gene from *pseudomonas putida* BH. Journal of Fermentation and Bioengineering 79(5):485–488, 1995.
Gasson. Progress and potential in the biotechnology of lactic acid bacteria. FEMS Microbiology Reviews. 12:3–20, 1993.
Darnell et al. Molecular Cell Biology, 2nd edition. Scientific American Books, Inc. pp. 231–240 and 249–253, 1990.
Proceedings of Environmental Engineering Research, vol. 33 (1996) Nakamura & Ishida, Development of a genetically engineered microorganism for trichloroethylene degradation . . . , pp. 165–175.

Journal of Bacteriology, vol. 178, No. 14, (Jul. 1996) Suyama et al, Engineering Hybrid Pseudomonads Capable of Utilizing a Wide Range of Aromatic Hydrocarbons . . . , pp. 4039–4046.

Applied and Environmental Microbiology, vol. 64, No. 1, (Jan. 1998) Yee et al, Rhizoremediation of Trichloroethylene by a Recombinant, Root–Colonizing *Pseudomonas fluorescens*. . . , pp. 112–118.

Applied and Environmental Microbiology, vol. 64, No. 7 (Jul. 1998) Berendes et al, Construction and Use of an ipb DNA Module to Generate *Pseudomonas Strains*. . . , pp. 2454–2462.

*Primary Examiner*—Robert A. Wax
*Attorney, Agent, or Firm*—Flynn, Thiel, Boutell & Tanis, P.C.

[57] ABSTRACT

The gene recombinant according to the present invention is capable of expressing a biodegradability for chlorinated ethylene and has a recombinant DNA sequence carried on a chromosome, which sequence comprises a phenol-hydroxylase gene originating from a phenol-metabolizable bacterium capable of bio-degrading chlorinated ethylene, wherein the phenol-hydroxylase gene comprises a gene for facilitating decomposition of chlorinated ethylene and a series of genes for decomposing chlorinated ethylene, and a promoter inserted upstream from the phenol-hydroxylase gene, and/or a terminator inserted downstream from the phenol-hydroxylase gene.

22 Claims, 6 Drawing Sheets

GENE RECOMBINANT WITH BIODEGRADABILITY FOR CHLORINATED ETHYLENE AND BIO-TREATMENT OF CHLORINATED ETHYLENE THEREWITH

FIELD OF THE INVENTION

The present invention relates to a gene recombinant with a recombinant DNA (in the context of this application this is often referred to only as "gene recombinant") capable of expressing a biodegradability for chlorinated ethylene under aerobic conditions and, in particular, to a gene recombinant of a bacteria of, such as, the genus Pseudomonas having this recombinant DNA as well as to a method for the biological treatment of chlorinated ethylene by such a recombinant.

BACKGROUND OF THE INVENTION

While trichloroethylene (TCE) has widely been used as solvent, it is toxic and difficult to decompose by natural microbes, whereby problems of the pollution of the soil and subterranean water therefrom have been brought about in various districts.

A technique has been proposed in WO89/09827 for decomposing TCE, in which a toluene-monoxygenase gene originating from *Pseudomonas mendocina* KR-1 and having a biodegradability for TCE is introduced into a host bacterial cell by a foreign plasmid and the bacteria having this recombinant gene is used to effect biodegradation of TCE. However, this recombinant is obtained by introduction of a toluene-monoxygenase gene by a foreign plasmid and the toluene-monoxygenase gene is not carried on the chromosome, so that the efficiency of the biodegradation of trichloroethylene is low.

A technique of the biodegradation of TCE using a recombinant by recourse also to the use of a foreign plasmid is reported in the Journal of Fermentation and Bioengineering, Vol. 79, No. 2, 100–106 (1995). This technique is based on the use of the phenol-hydroxylase gene of *Pseudomonas putida* BH. However, this recombinant also exhibits a low capacity for decomposing chlorinated ethylene per unit cell population of as low as about 7.5 mg/liter·$A_{600}$ ($A_{600}$ is an absorbancy at 600 nm and serves as a parameter for the bacterial cell concentration). It is taught therein that the phenol-hydroxylase gene of *Pseudomonas putida* BH is composed of several components. It is also indicated in J. Ferment. and Bioeng., Vol. 79, No. 5, 485–488 (1995) that the phenol-hydroxylase gene of *Pseudomonas putida* BH is composed of several components.

In Japanese Patent Kokai Hei-6-105691 A, it is described that the phenol-hydroxylase (hereinafter sometimes abbreviated as PH) which is originated from the chromosomal DNA of the cell strain *Pseudomonas putida* KWI-9 decomposes trichloroethylene. Herein is described that a recombinant is prepared by introducing into the host cell a recombinant DNA having the PH gene and, downstream thereof, a terminator connected thereto, by a foreign plasmid. However, the capability of this recombinant for decomposing chlorinated ethylene is not sufficient, since the recombinant DNA is carried on the foreign plasmid.

Afterwards, it was confirmed by research at the gene level for the PH that the minimum unit of the PH gene for trichloroethylene-biodegradability consists of a group of chlorinated ethylene decomposing genes composed of 5 genes represented as pheA, pheB, pheC, pheD and pheE and that a gene for facilitating decomposition of chlorinated ethylene, which is denoted as pheZ, is present upstream from them. This bacteria *Pseudomonas putida* KWI-9 has the PH gene on the chromosomal DNA and exhibits a capability for biodegradation of chlorinated ethylene, though at a low level.

In Report of Environmental Engineering, Vol. 33, 165–175 (1996), a technique is given in which a tac-promotor is inserted upstream of the PH gene on the chromosome of the cell strain *Pseudomonas putida* KWI-9 to formulate a recombinant (*Pseudomonas putida* KN1-10A) which is used for biodegradation of trichloroethylene. However, this recombinant exhibits a low capacity for the biodegradation of chlorinated ethylene per unit cell population, since a promoter is inserted within the gene for facilitating decomposition of chlorinated ethylene, i.e. pheZ, and thus, the function of pheZ is obstructed.

Thus, recombinants of the prior art exhibit lower capabilities for decomposing chlorinated ethylene due to blocking of the function of the gene pheZ which facilitates decomposition of chlorinated ethylene or because of a biodegradability based on the function of a foreign plasmid, so that there has been a request for an improvement in the biodegradability for chlorinated ethylene.

SUMMARY OF THE INVENTION

Therefore, an object of the present invention is to provide a gene recombinant capable of expressing a high biodegradability for chlorinated ethylene.

Another object of the present invention is to provide a method of biological treatment of chlorinated ethylene, in which the chlorinated ethylene is decomposed efficiently by biodegradation under aerobic conditions.

The gene recombinant capable of expressing a biodegradability for chlorinated ethylene according to the present invention, comprises a recombinant DNA sequence carried on the chromosome, which sequence comprises
a phenol-hydroxylase gene originated from a phenol-metabolizable bacterium capable of biodegrading chlorinated ethylene, wherein the phenol-hydroxylase gene comprises a gene for facilitating decomposition of chlorinated ethylene and a series of genes for decomposing chlorinated ethylene, and
a promoter inserted upstream from the phenol-hydroxylase gene.

The gene recombinant capable of expressing a biodegradability for chlorinated ethylene may also comprise a recombinant DNA sequence carried on the chromosome, which sequence comprises
a phenol-hydroxylase gene originating from a phenol-metabolizable bacterium capable of biodegrading chlorinated ethylene, wherein the phenol-hydroxylase gene comprises a gene for facilitating decomposition of chlorinated ethylene and a series of genes for decomposing chlorinated ethylene, and
a terminator inserted downstream from the phenol-hydroxylase gene.

The method of biological treatment of chlorinated ethylene according to the present invention comprises subjecting the chlorinated ethylene to biological digestion by the above-mentioned gene recombinant.

DETAILED DESCRIPTION OF THE INVENTION

The First Gene Recombinant

The first gene recombinant is a gene recombinant bacterium in which a recombinant DNA having inserted therein a promoter upstream of the phenol-hydroxylase gene is held on the chromosome. With such a gene-recombinant, chlorinated ethylene is decomposed by biodegradation by the phenol-hydroxylase.

For the phenol-hydroxylase gene, there may be used a phenol-hydroxylase gene originating from a phenol-metabolizable bacterium having a biodegradability for chlorinated ethylene, which comprises a gene for facilitating decomposition of chlorinated ethylene (CE decomposition-facilitating gene) and a chlorinated ethylene-decomposable gene group (CE decomposing gene).

As the phenol-metabolizable bacteria having the biodegradability for chlorinated ethylene, there may be exemplified *Pseudomonas putida* KWI-9, *Pseudomonas putida* BH, *Alkaligenes eutrophus* JMP 134 (Applied and Environmental Microbiology, Vol. 62, No. 9, 3227–3233 (1996)) and others.

Among these phenol-metabolizable bacteria, preference is given for *Pseudomonas putida* KWI-9.

Figure 1:
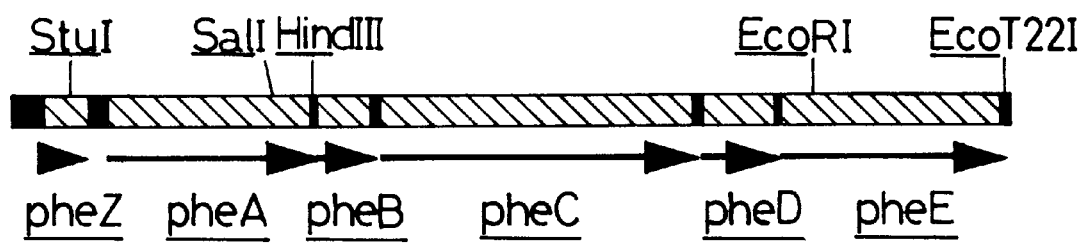
FIG. 1 is a gene constructional diagram showing the organization of the phenol-hydroxylase gene of *Pseudomonas putida* KWI-9.

The PH gene existing in the chromosomal DNA of *Pseudomonas putida* KWI-9 is a gene group comprising a CE decomposing gene composed of 5 minimum units, pheA, pheB, pheC, pheD and pheE and, upstream thereof, a CE decomposition-facilitating gene pheZ. The gene arrangements for pheZ, pheA, pheB, pheC, pheD and pheE of *Pseudomonas putida* KWI-9 are given in SEQ ID NO: 1. The gene organizations of them are shown in FIG. 1.

The cell strain of *Pseudomonas putida* KWI-9 has been deposited at the Fermentation Research Institute Agency of Industrial Science and Technology with a Receipt No. FERM BP 6356 and the bacterial nature, method of culture thereof and so on are disclosed in Japanese Patent Kokai Hei-6-70753.

As the promoter to be inserted into the gene upstream of the PH gene group, one which has a capability for bringing about a constitutive expression within the objective cell to be subjected to the recombination of the gene may favorably be employed. Specific examples of a promoter capable of bringing about such a constitutive expression include lac- and trp-promotors originating from *E. coli* and tac-promotors synthesized therefrom. Among them, preference is given for the tac-promotors.

The promoter may preferably be inserted into the DNA sequence upstream from the PH gene group at a position close thereto and, for example, at a position remote from the PH gene group by a distance in terms of number of base pair of, for example, 1–3,000, preferably 1–500.

The recombinant DNA having inserted upstream of the PH gene group a promoter may preferably have, inserted downstream from the PH gene group, a terminator. When the chlorinated ethylene-decomposing gene group originates from *Pseudomonas putida* KWI-9, it is preferable that a terminator is inserted therein at a position downstream from the gene pheE.

Such a terminator may favorably be inserted into the recombinant DNA downstream from the PH gene group at a position as close to the PH gene group as possible, for example, at a position remote from the PH gene group by a distance in terms of number of base pair of 1 to 3,000, preferably 1 to 500.

As the terminator, those which express a function of terminating gene transcription at least partly may be employed without any limitation. Specifically, use of terminators having a stem-and-loop structure may be used generically, though others including rho dependent terminators and combinations of an operator with a protein combined thereto may also be used. Specific examples of terminators having a stem-and-loop structure include terminator $rrnBT_1T_2$ 5SrRNA originating from *Escherichia coli* and trpA transcription terminator.

The objective bacteria to be subjected to the gene recombination by inserting the recombinant DNA sequence into the chromosomal gene chain are not specifically restricted, while a bacterium of the genus Pseudomonas, in particular *Pseudomonas putida* KWI-9 may preferably be used therefor. When using *Pseudomonas putida* KWI-9, a first gene recombinant according to the present invention is obtained by inserting a promoter into the chromosomal DNA thereof at a position upstream of the PH gene group. For example, the following procedures may specifically be implemented.

A DNA fragment of a length of several thousands base pairs at a position before and after the initiation point of the PH gene group is first inserted into a plasmid vector having a conjugative ability. Then, the promoter can be inserted therein by making use of the cleavage site for a restriction enzyme existing upstream of the initiation point of the PH gene group. The so-prepared recombinant plasmid is then inserted into a bacterial cell of, for example, *E. coli* S17-1 strain, whereupon it is conjugated with *Pseudomonas putida* KWI-9 on a filter to effect a homologous recombination. Having been prepared in this manner, a gene recombinant having on its chromosome the above-mentioned recombinant DNA including the inserted promoter is selectively separated. When a DNA fragment having a capability for terminating gene transcription is to be inserted, a terminator can be inserted therein by making use of a restriction enzyme cleavage site existing downstream of the gene pheE, such as the portion of pheF, either before or after the insertion of the promoter.

Also in the case where the objective bacteria to be subjected to recombination of the gene are other than *Pseudomonas putida* KWI-9, a first gene recombinant according to the present invention can be prepared in a similar way as above, so long as the objective bacteria have a PH gene group on their chromosomes.

When the objective bacteria do not have any PH gene, one can obtain a first gene recombinant according to the present invention by first inserting into the chromosome of the bacteria a recombinant DNA having a promoter inserted therein upstream of the PH gene group. In actual practice, for example, the following procedures may be performed.

A recombinant DNA having a promoter with a subsequent PH gene group is first inserted into the chromosome using a transposon. When a DNA fragment having a capability for terminating gene transcription should also be inserted therein, a recombinant DNA having a promoter and a PH gene group with a subsequent terminator is inserted into the chromosome using a transposon. As the vector containing such a transposon, there may be employed, for example, pUT/Km, pLOF/Km and so on (See Journal of Bacteriology, Vol. 172, No. 11, 6557–6567 (1990)).

The PH gene group in *Pseudomonas putida* KWI-9 can be isolated therefrom by a technique known per se using a restriction enzyme. A specific practice thereof is given in Japanese Patent Kokai Hei-6-105691 A in detail. Since the nucleotide sequence of the PH gene group is known as shown in SEQ ID NO: 1, it can be synthesized by Polymerase Chain Reaction (PCR) using the chromosome of *Pseudomonas putida* KWI-9 as the template.

The first gene recombinant according to the present invention carries the recombinant DNA having a promoter inserted therein upstream of the CE decomposition-facilitating gene (e.g. pheZ) of the PH gene group on the chromosome intrinsic to the original bacteria, so that the CE decomposition-facilitating gene and the CE decomposing gene are constitutively expressed, whereby the biodegradability of the resulting gene recombinant for chlorinated ethylene per unit cell population is high.

The first gene recombinant according to the present invention may carry the recombinant DNA also on the intrinsic plasmid in addition to that carried on the chromosome. When the CE decomposition-facilitating gene and the CE decomposing gene are coded on the gene in the plasmid included intrinsically in the original bacterium, the biodegradability of the gene recombinant for chlorinated ethylene can be increased by inserting a promoter into the gene of the bacterium-intrinsic plasmid, since the so obtained "recombinant plasmid" is held stable in the bacterial cell as contrasted to the foreign plasmid. On the other hand, when a foreign plasmid in which the above-mentioned recombinant DNA is integrated is introduced in the objective bacteria, the so-obtained bacteria may exhibit lower biodegradability for chlorinated ethylene, since the foreign plasmid is not stable in the bacterial cell.

The Second Gene Recombinant

The second gene recombinant according to the present invention has a chromosome integrated with a recombinant DNA obtained by inserting a terminator into a DNA sequence having a phenol-hydroxylase gene at a position downstream from this phenol-hydroxylase gene. With such a gene recombinant, chlorinated ethylene can be decomposed by biodegradation due to the phenol-hydroxylase.

As the phenol-hydroxylase gene, one which originates from a phenol-metabolizable bacterium having a biodegradability for chlorinated ethylene and which comprises a CE decomposition-facilitating gene and a CE decomposing gene group may be used. This phenol-hydroxylase gene is the same as that in the first gene recombinant described above.

As the phenol-metabolizable bacterium having a biodegradability for chlorinated ethylene, those which are used in the first gene recombinant according to the present invention given above may be used. A preferable one is *Pseudomonas putida* KWI-9, which is as described above for the first gene recombinant. When the phenol-hydroxylase gene originates from *Pseudomonas putida* KWI-9, it is preferable that a terminator is inserted downstream from the gene pheE.

The terminator may preferably be present in the recombinant DNA sequence at a position downstream from the CE decomposing gene (for example pheE) as close thereto as possible and, for example, at a distance therefrom of 1–3,000, preferably 1–500 bp.

As the terminator, those which express the function of terminating gene transcription at least partly may be employed without any limitation. Specifically, use of terminators having a stem-and-loop structure may be used generically, though others including rho dependent terminators and combinations of an operator with a protein combined thereto may also be used. Specific examples of terminators having a stem-and-loop structure include terminator rrnBT$_1$T$_2$ of 5SrRNA originated from *Escherichia coli* and trpA transcription terminator.

For the recombinant DNA sequence, those which contain a promoter inserted therein at an upper reach from the CE decomposing gene are preferred. As the promoter to be inserted into the gene in the upstream of the PH gene group, one which has a capability for bringing about a constitutive expression within the objective bacterial cell to be subjected to the gene recombination may favorably be employed. Specific examples of a promoter capable of bringing about such a constitutive expression include lac- and trp-promoters and tac-promoters synthesized therefrom. Among them, preference is given for the tac-promoters.

When the chlorinated ethylene-decomposing gene originates from *Pseudomonas putida* KWI-9, it is preferable that a promoter is present at a position upstream from the CE decomposition-facilitating gene pheZ.

The promoter may preferably be inserted into the DNA sequence at a position upstream from the CE decomposing gene as close thereto as possible and, for example, at a distance therefrom in terms of number of base pair of, for example, 1–3,000, preferably 1–500.

The objective bacteria to be subjected to the gene recombination by inserting the recombinant DNA sequence into the chromosomal gene chain are not specifically restricted, while a bacterium of the genus Pseudomonas, in particular *Pseudomonas putida* KWI-9 may preferably be used therefor. When using *Pseudomonas putida* KWI-9, a second gene recombinant according to the present invention is obtained by inserting a terminator into the chromosomal DNA thereof at a position downstream from the CE decomposing gene pheE. For example, the following procedures may specifically be implemented.

A DNA fragment of a length of several thousands base pairs at a position before and after the termination point of the CE decomposing gene pheE is first inserted into a plasmid vector having a conjugative ability. Then, a terminator can be inserted therein by making use of the cleavage site for a restriction enzyme existing downstream from the gene pheE, for example, at pheF. The so-prepared recombinant plasmid is then inserted into a bacterial cell of, for example, *E. Coli* S17-1 strain, whereupon it is conjugated with *Pseudomonas putida* KWI-9 on a filter to effect a homologous recombination. Having been prepared in this manner, a gene recombinant having on its chromosome the above-mentioned recombinant DNA including the inserted terminator is selectively separated.

In the case where the objective bacteria to be subjected to recombination of the gene are other than *Pseudomonas*

*putida* KWI-9, a second gene recombinant according to the present invention can be prepared in a similar way as above, so long as the objective bacteria have a CE decomposing gene on their chromosomes.

When the objective bacteria do not have any CE decomposing gene, one can obtain the second gene recombinant according to the present invention by first inserting into the chromosome of the bacteria a recombinant DNA having a terminator inserted therein downstream from the CE decomposing gene. In actual practice, for example, the following procedures may be performed.

A recombinant DNA having a CE decomposing gene and subsequent terminator is first inserted into the chromosome using a transposon. As the vector containing the transposon, there may be employed, for example, pUT/Km, pLOF/Km and so on (See J. Bacteriology, Vol. 172, No. 11, 6557–6567 (1990)).

In the second gene recombinant according to the present invention, the intrinsic chromosome of the original objective bacterium is integrated with the recombinant DNA having an inserted terminator at a position downstream from the CE decomposing gene (for example pheE) so that the biodegradability of the resulting gene recombinant for chlorinated ethylene per unit cell population is increased. The actual basis of such an increase in the biodegradability is not certain, but it is assumed that any protein synthesis unnecessary for decomposing chlorinated ethylene is avoided due to the exclusion of the transcription of genes downstream from the CE decomposing gene, resulting in an exclusion of the useless consumption of energy and, thus, sparing the energy for consumption in the biodegradation of chlorinated ethylene.

The second gene recombinant according to the present invention may have the recombinant DNA mentioned above not only in the chromosomal gene sequence but also in the gene sequence of the plasmid intrinsic to the original bacterium. When the CE decomposing gene is coded in the gene sequence of the intrinsic plasmid, the biodegradability of the gene recombinant for chlorinated ethylene per unit cell population can be increased by inserting a DNA fragment expressing a function of terminating gene transcription into the gene sequence of the intrinsic plasmid, since the resulting "recombinant plasmid" is held stable in the bacterial cell, as contrasted to that of a foreign plasmid. In contrast thereto, when a foreign plasmid in which the above-mentioned terminator is integrated with the plasmid gene sequence at a position downstream from the CE decomposing gene is introduced in the objective bacterium, the so-obtained gene recombinant bacterium may exhibit a lower biodegradability for chlorinated ethylene per unit cell population since this foreign plasmid is unstable in the bacterial cell.

Specific compounds of chlorinated ethylene (CE) which can be decomposed by biodegradation by the first and the second gene recombinants according to the present invention include trichloroethylene (TCE), cis-1,2-dichloroethylene, trans-1,2-dichloroethylene, 1,1-dichloroethylene, vinyl chloride and mixtures of them.

Practice for Biodegradation of CE

For effecting the biodegradation of chlorinated ethylene using the first or the second gene recombinant, various techniques may be employed, for example, an aerobic culture of the first or the second gene recombinant according to the present invention in a culture medium containing the chlorinated ethylene and the like, whereby the chlorinated ethylene can completely be dechlorinated.

The culturing of the first or the second gene recombinant according to the present invention is carried out under a condition adapted for the growth of the gene recombinant. When the gene recombinant is *Pseudomonas putida* KWI-9, it is preferable to carry out the culturing using a carbon source and a nitrogen source, such as peptone, tripton and yeast extract, as well as inorganic salts, such as sodium chloride and potassium chloride, under an aerobic condition at a pH of 5–8.5, preferably 6–7, and a temperature of 15–35° C., preferably around 30° C.

As explained above, the first gene recombinant according to the present invention has a high biodegradability for chlorinated ethylene per unit cell population due to the gene structure in which a recombinant DNA sequence originating from a phenol-metabolizable bacterium and having a phenol-hydroxylase gene expressing a biodegradability for chlorinated ethylene with a promoter inserted at a position upstream of the phenol-hydroxylase gene is held on the chromosome.

The second gene recombinant according to the present invention has a high biodegradability for chlorinated ethylene due to its gene structure in which a recombinant DNA sequence having a terminator inserted therein at a position downstream from the CE decomposing gene is held on the chromosome.

By the method for biological treatment of chlorinated ethylene according to the present invention, a high yield of decomposition of the chlorinated ethylene can be attained due to the use of the above-mentioned gene recombinant.

PREFERRED EMBODIMENT OF THE INVENTION

Below, the invention will further be described in more detail by way of Examples and Comparative Examples, wherein Examples 1 to 3 and Comparative Examples 1 and 2 refer to the first gene recombinant according to the present invention and Examples 3 and 4 and Comparative Example 3 refer to the second gene recombinant according to the present invention. The gene recombinant used in Example 3 corresponds not only to the first gene recombinant but also to the second gene recombinant according to the present invention. The plasmids and the microorganism employed in Examples were as given below:

*Pseudomonas putida* KWI-9

This is a phenol-metabolizable but not toluene-metabolizable cell strain having a biodegradability for chlorinated ethylene and has been deposited under the Receipt Number given previously. The biodegradability thereof for chlorinated ethylene is obstructed considerably by the co-existence of phenols.

*E. coli* S17-1 Strain

This is an *Escherichia coli* having an IncP plasmid RP4 intrinsically on the chromosome. A method for its preparation is given in BIO/TECHNOLOGY, 1, 784–791 (1983). This has been deposited at the Department of Agriculture, Northern Regional Research Center (Accession No. B-15483, U.S. Pat. No. 4,680,264).

*E. coli* HB101

This is marketed from Toyobo Co., Ltd. as a competent cell.

pTrc99A

This is a derivative of a protein expressing vector pKK233-2 (a product of the firm Pharmacia with a product code No. 27-4935-01). This plasmid is marketed from Pharmacia with a product code No. 27-5007-01.

EXAMPLE 1 AND COMPARATIVE EXAMPLE 1

1. Preparation of *Pseudomonas putida* KN1-200A

Figure 2:
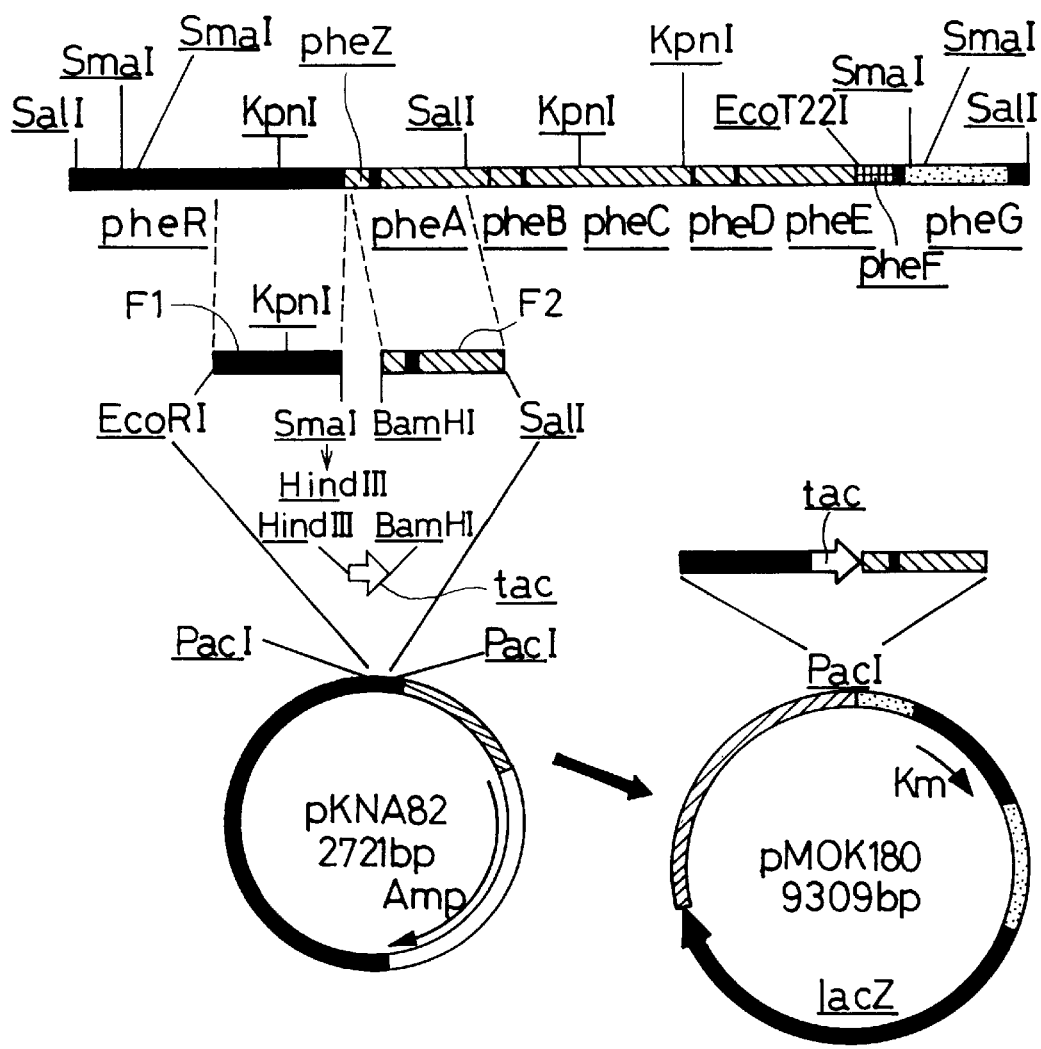
FIG. 2 shows the process course of the insertion of the homologous part required for inserting the gene group (pheR to pheG) of phenol-hydroxylase and the tac-promotor into pKNA82 by a schematic gene map.

The phenol-hydroxylase gene group exhibiting biodegradability for chlorinated ethylene coded on the chromosome of *Pseudomonas putida* KWI-9 is shown in FIG. 2 as a gene map. The essential gene unit necessary for attaining biodegradation of chlorinated ethylene comprises five gene units pheA to pheE (CE decomposing gene group). The gene unit pheZ found upstream from pheA is the CE decomposition-facilitating gene. Upstream from pheZ, a tac-promotor was inserted by the procedures given below. *Pseudomonas putida* KN1-200A employed in Example 1 was prepared by a homologous recombination as given below (See FIG. 2).

1) Preparation of the Homologous Part in the Upstream of pheZ Necessary for Homologous Recombination Using the primer pair given below and using the chromosome of *Pseudomonas putida* KWI-9 as the template, a sequence of a length of 1.1 kb upstream of the gene pheZ was synthesized by PCR.

Upper Primer: 5'-GGG <u>GAA TCC</u> GGG GGA GGG GGT AAG GGG GTG GTG-3' (SEQ ID NO: 2)

Lower Primer: 5'-GGG <u>CCC GGG</u> AAG AGC GTG CCA GCT GGC GCA AAC-3' (SEQ ID NO: 3)

(the underlined portion of the upper primer indicates the site of EcoRI and that in the lower primer indicates the site of SmaI).

2) Insertion of PCR-synthesized Homologous Part of 1.1 kb EcoRI-SmaI Fragment (FIG. 3) into pKNA82

The homologous 1.1 kb EcoRI-SmaI fragment part (a fragment indicated by a symbol F1 in FIG. 2) synthesized by PCR was inserted into a plasmid vector pKNA82 at the portion of EcoRI-SmaI thereof.

3) Preparation of Homologous Part including pheZ and a Part of pheA necessary for Homologous Recombination Using the primer pair given below and using *Pseudomonas putida* KWI-9 as the template, pheZ and pheA were prepared by PCR.

Upper Primer: 5'-GGG <u>GGA TCC</u> CGC AAT AGA GGC CAT ACC GCC CA-3' (SEQ ID NO: 4)

Lower Primer: 5'-CGC <u>GGA TCC</u> GGC GGT TTC CTC AGG CGG CAA GGC-3' (SEQ ID NO: 5)

(the underlined portion of the upper primer indicates the site of BamHI)

The synthesized DNA fragment was subjected to digestion by BamHI and SalI and the thereby obtained 1 kb BamHI-SalI fragment starting from the initiation point of pheZ to the position of SalI in pheA (the fragment indicated by the symbol F2 in FIG. 2) served as another homologous part.

4) Insertion of Synthesized 1 kb BamHI-SalI Fragment Homologous Part into pKNA82

The PCR-synthesized homologous 1 kb BamHI-SalI fragment part (F2) was inserted into the BamHI-SalI site of pKNA82 subsequent to the already inserted EcoRI-SmaI fragment (F1).

5) Insertion of tac-Promotor into SmaI-BamHI Site in Between the Homologous Fragments In the pKNA82 having inserted therein two fragments F1 and F2, a HindIII linker {(d(pCAAGCTTG)} was inserted at its SmaI site of the right terminal end of the homologous part of the left fragment (F1). Then, this plasmid was cleaved using HindIII and BamHI and the cleavage was re-combined by inserting thereinto a tac-promotor as given below (a double stranded DNA, of which one DNA strand is given) excised by HindIII and BamHI.

5'-AAG CTT ACT CCC CAT CCC CCT GTT GAC AAT TAA TCA TCG GCT CGT ATA ATG TGT GGA ATT GTG AGC GGA TAA CAA TTT CAC ACA GGA AAC AGG ATC C-3' (SEQ ID NO: 6)

(The underlined portions indicate the sites of HindIII and BamHI, respectively).

6) Insertion of Homologous Part Containing a tac-Promotor into pMOK180

The homologous part containing a tac-promotor was excised using PacI and was inserted into pMOK180 at its PacI site as shown in FIG. 2. The so-constructed plasmid was introduced into *E. coli* S17-1 cell strain and the resulting bacterium was caused to conjugate with *Pseudomonas putida* KWI-9 in such a manner as given in 7) below to effect a homologous recombination. By this, a gene recombinant *Pseudomonas putida* KN1-200A was obtained, in which the tac-promotor has been inserted in the chromosome upstream from the gene pheZ thereof, which was then separated selectively.

7) Insertion into the Chromosome

On carrying out the homologous recombination, the plasmid pMOK180 containing the tac-promotor, prepared as in 6) above, was introduced into a doner bacterium *E. coli* S17-1, whereupon it was cultured in an LB liquid culture medium (10 g of tripton, 5 g of yeast extract and 5 g of NaCl were dissolved in 1 liter of distilled water) overnight at 37° C. Parallel therewith, a receptor bacterium of *Pseudomonas putida* KWI-9 strain was cultured in an LB medium at 30° C. overnight. Each 0,5 ml of culture liquor was taken out from these cultures and the bacterial cells therein were collected on a centrifuge.

The so-collected cells of both bacteria were resuspended together in 1 ml of physiological saline (0.8% NaCl) and mixed, whereupon they were collected again in a centrifuge and the supernatant was discarded and the cells were washed with 1 ml of physiological saline. This washing procedure was repeated again and the bacterial cells were settled, whereupon the resulting bacterial mixture was suspended in 50 µl of physiological saline. This suspension was dropped onto a sterilized millipore filter of 25 mm diameter having an average pore size of 0.22 µm placed on an LB culture medium, in order to cause conjugation for a period of time of 10 hours at 30° C. Then, the bacterial cells on the filter were taken out and suspended in 1 ml of physiological saline. The suspension was spread, after dilution, on an agar medium containing inorganic salts, 20 mM fructose and 100 µg/ml of kanamycin. The agar medium was subjected to culturing for 3–4 days at 30° C., whereupon the cell strain in which the above-mentioned plasmid gene had been integrated in the chromosomal gene was separated selectively.

8) Selective Separation of *Pseudomonas putida* KN1-200A

The cell strain obtained in 7) above was cultured in an LB liquid culture medium overnight. A diluted culture liquor was spread on an LB agar medium containing 20 μg/ml of XGal (namely, 5-bromo-5-chloro-3-indoyl-β-D-galactoside) to develop colonies of the bacterium. White colonies found among the blue colonies were separated selectively as the cell strain in which pMOK180 had been deleted. Among them, a cell strain which turned yellow when sprayed with 0.1 M catechol (due to expression of pheF which codes catechol-2,3-oxygenase by the function of the tac-promotor) was selected as *Pseudomonas putida* KN1-200A which has a tac-promotor inserted upstream from pheZ.

Figure 3:
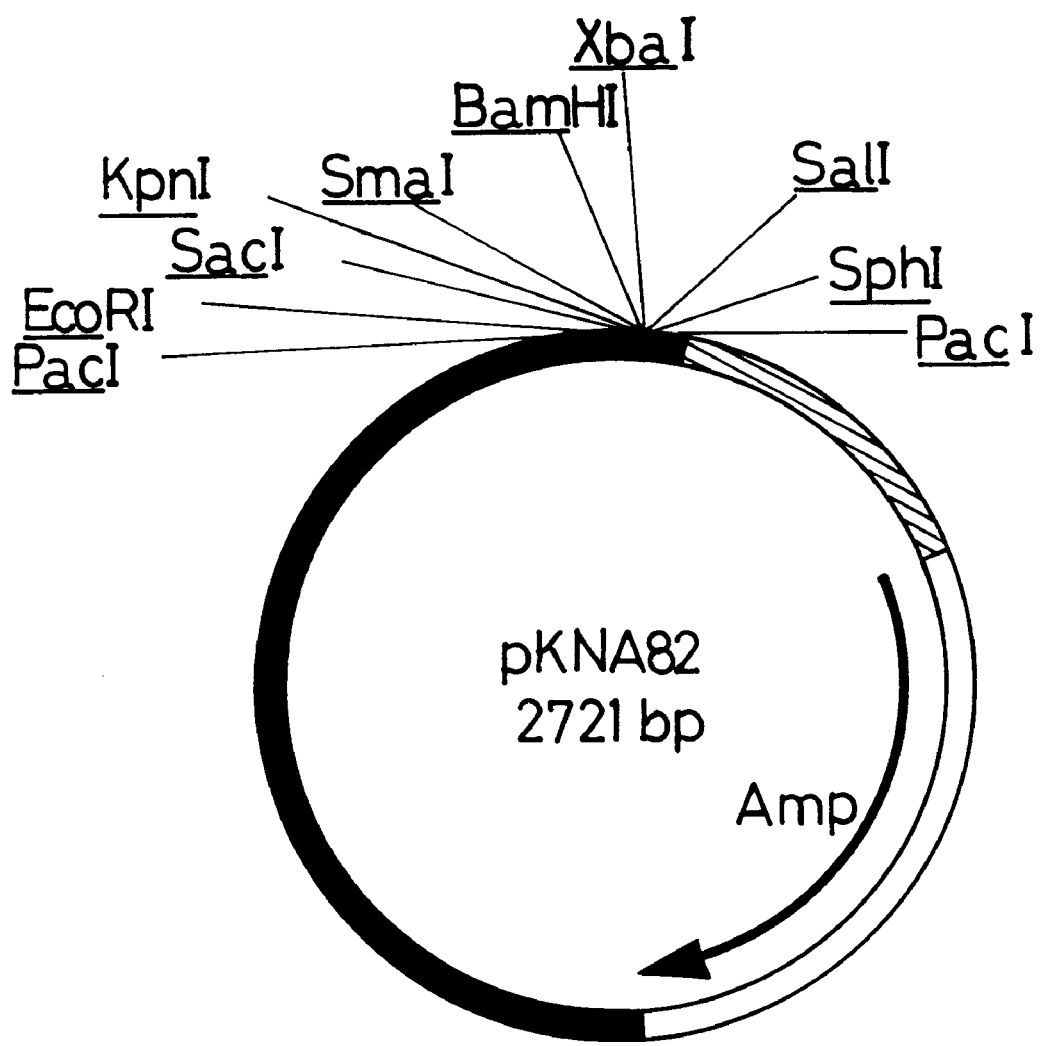
FIG. 3 shows the site of the plasmid pKNA82 scissored by a restriction enzyme in a schematic gene map.

9) Construction of pKNA82 (Cf. FIG. 3)

This pKNA82 was synthesized in the manner as follows: Thus, the promoter portions of lacIq and trc of pTrc99A supplied from the firm Pharmacia were excised using EcoT22I and NcoI to remove it and the resulting fragment was treated with T4 polymerase to flatten both ends, whereupon a PacI linker {d(pTTAATTAA)} was inserted therebetween. The above-mentioned plasmid was cleaved at the site of HindIII within the multicloning site thereof using HindIII, followed by a treatment with T4 polymerase to flatten both ends and another PacI linker {d(pGTTAATTAAC)} was inserted therebetween. This plasmid was identified as pKNA82.

10) Construction of pMOK180

This pMOK180 was constructed in accordance with the method reported in Environmental Engineering Research Reports, Vol. 33, 165–175 (1996) in the following manner. Thus, an ori-gene originating from pBR322 was employed and, as the gene requisite for the mobilization, mobA, mobB and oriT of pKT240 were used. For the marker, a fragment containing a gpt-promoter and lacZ originated from pCH110 was used.

2. Biodegradation Test for Chlorinated Ethylene

Using the gene recombinant obtained as above, biodegradation tests for trichloroethylene (TCE) were carried out as follows:

1) Cell Strains Employed

*Pseudomonas putida* KN1-200A: The gene recombinant obtained as above, which was used in Example 1.

*Pseudomonas putida* KN1-10A: A gene recombinant in which a tac-promoter is held inserted into pheZ of *Pseudomonas putida* KWI-9, so as to cause the TCE biodegradation constitutively. In this gene recombinant, the function of pheZ is excluded due to the insertion of the tac-promoter into the gene pheZ. This gene recombinant was synthesized in accordance with the method reported in Environmental Engineering Search Reports, Vol. 33, 165–175 (1996) and was used in Comparative Example 1.

2) TCE Biodegradation Tests

From a culture colony of the above gene recombinant, cells were taken out and planted in 5 ml of an LB liquid culture medium and were cultured overnight, whereupon a part of the culture liquor was transferred to 100 ml of an LB liquid culture medium. After having been cultured for more than 10 hours, the bacterial cells were collected in a centrifuge at the point of time at which $OD_{600}$ was reached at 0.5–1.5. The so-collected cells were washed with a mineral culture medium and were then collected again. The resulting cells were suspended in 10 ml of a mineral culture medium in a 125 ml glass vial so as to adjust the cell concentration at a value at which $OD_{600}$ equals 2.0. After addition of TCE thereto, shaking of the vial was started at a temperature of 30° C., whereupon the temporal change of the TCE concentration was pursued. When consumption of the originally added TCE due to the biodegradation was observed, an additional amount of TCE was replenished.

For the mineral culture medium, the following was employed.

| oMineral Culture Medium: | | |
|---|---|---|
| $Na_2HPO_4$ + $KH_2PO_4$ (1 M, pH 6.8) | | 40 ml |
| Huntner's vitamin-free mineral base | | *1)0.4 ml |
| $(NH_4)_2SO_4$ | | 1 g |
| Distilled water | | 840 ml |
| *1) Huntner's vitamin-free mineral base: | | |
| Nitrilotriacetic acid | | 10.0 g |
| $MgSO_4$ | | 14.45 g |
| $CaCl_2.2H_2O$ | | 3.335 g |
| $(NH_4)_6Mo_7O_{24}.4H_2O$ | | 9.25 mg |
| $FeSO_4.7H_2O$ | | 99 mg |
| Metals "44" *2) | | 50 ml |
| Distilled water | | to fill up to 1,000 ml |
| *2) Metals "44": | | |
| Ethylenediamine tetraacetate | | 250.0 mg |
| $ZnSO_4.7H_2O$ | 1,095.0 mg | (Zn 250 mg) |
| $FeSO_4.7H_2O$ | 500.0 mg | (Fe 100 mg) |
| $MnSO_4.H_2O$ | 154.0 mg | (Mn 50 mg) |
| $CuSO_4.5H_2O$ | 39.2 mg | (Cu 10 mg) |
| $Co(NO_3)_2.6H_2O$ | 24.8 mg | (Co 5 mg) |
| $Na_2B_4O_7.10H_2O$ | 17.7 mg | (B 2 mg) |
| a few drops of sulfuric acid for preventing any deposition | | |
| Distilled water | 100 ml | |

3) Test Results

Figure 4:
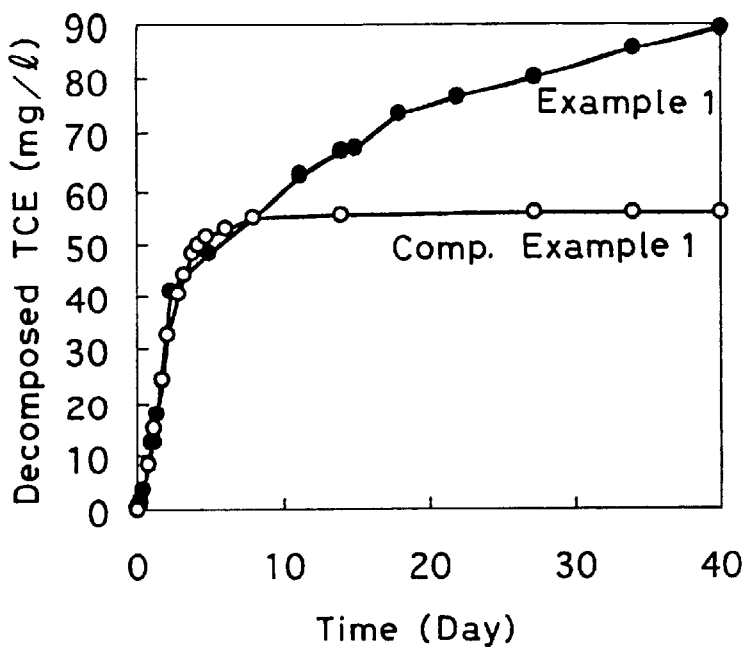
FIG. 4 is a graph showing the results of Example 1 and Comparative Example 1.

The observed temporal change in the amount of consumption of TCE (given as cumulative amount) by the biodegradation by the gene recombinants of Example 1 and Comparative Example 1, respectively, is shown in the graph of FIG. 4.

As seen in FIG. 4, while the biodegradabilities for the gene recombinant *Pseudomonas putida* KN1-200A (Example 1) in which a tac-promotor is held inserted upstream from pheZ of *Pseudomonas putida* KWI-9 and for the gene recombinant *Pseudomonas putida* KN1-10A (Comparative Example 1) in which the function of pheZ is destroyed, respectively, are almost the same up to about the $9^{th}$ day, their biodegradabilities for TCE become different thereafter in such a manner that the TCE decomposition continues to proceed with *Pseudomonas putida* KN1-200A, whereas, for *Pseudomonas putida* KN1-10A, no progress of TCE decomposition is seen thereafter, so that the TCE decomposition by the former amounts to 1.7 times that by the latter after 40 days.

From the above, it was proven that a gene recombinant exhibiting a higher biodegradability for TCE can be prepared by introducing in the chromosome of a phenol-metabolizable bacterium with a PH gene having a TCE decomposition-facilitating gene, i.e. pheZ, at an upper reach from pheZ, a promoter including a constitutive expression.

Example 2 and Comparative Example 2

Biodegradability tests were carried out using cell strains given below, in which the pheZ-containing PH gene was introduced using a foreign plasmid.

1) Cell Strains Employed

*Pseudomonas putida* KN1-200A: The same as that in

Example 1

*Pseudomonas putida* KN1 (pNIN205): This is a transformant synthesized by introducing a PH gene into the plasmid pRCT200 which have been integrated with a trc-promoter (this has the same function with tac-promoter) at the multicloning site thereof to obtain pNIN205, followed by introduction of this plasmid into *Pseudomonas putida* KWI-9. Details therefor are given below. This was used in Comparative Example 2.

2) Preparation of *Pseudomonas putida* KN1 (pNIN205)

The above transformant used in Comparative Example 2 was prepared in the manner as follows:

A gene sequence starting, in the gene units of phenol-hydroxylase shown in FIG. 2, from pheZ to pheE was excised and was integrated with pRCT200 which includes constitutive expression, at the multicloning site thereof using a trc-promotor. Here, the PCR-synthesized portion given in FIG. 2 was utilized for the sequence starting from the gene pheZ to SalI in the gene pheA, in order to introduce BamHI into the gene sequence on the side at the 5'-end of pheZ. The site of EcoT22I was treated with T4 polymerase to flatten it and an XbaI linker {d(pCTCTAGAG)} was inserted therebetween, so that the gene sequence starting from pheZ to pheE can be excised using BamHI and XbaI.

The excised gene sequence from pheZ to pheE was inserted into pRCT200 at the portion from BamHI to XbaI of the multicloning site thereof. This recombinant plasmid was identified as pNIN205. At a position upstream from the multicloning site of pNIN205, there is integrated originally a trc-promotor, so that the inserted gene sequence starting from pheZ to pheE will be expressed constitutively. Downstream from the multicloning site of pNIN205, a terminator $rrnBT_1T_2$ is integrated originally, the transcription of the gene will terminate at this position. This pNIN205 was introduced into *Pseudomonas putida* KN1 by electroporation to obtain the transformant *Pseudomonas putida* KN1 (pNIN205). The above-mentioned pRCT200 was synthesized in accordance with the method given in Example 3 in Japanese Patent Kokai Hei-6-105691.

3) TCE Biodegradation Tests

The procedures of the test were the same as in Example 1.

4) Test Results

Figure 5:
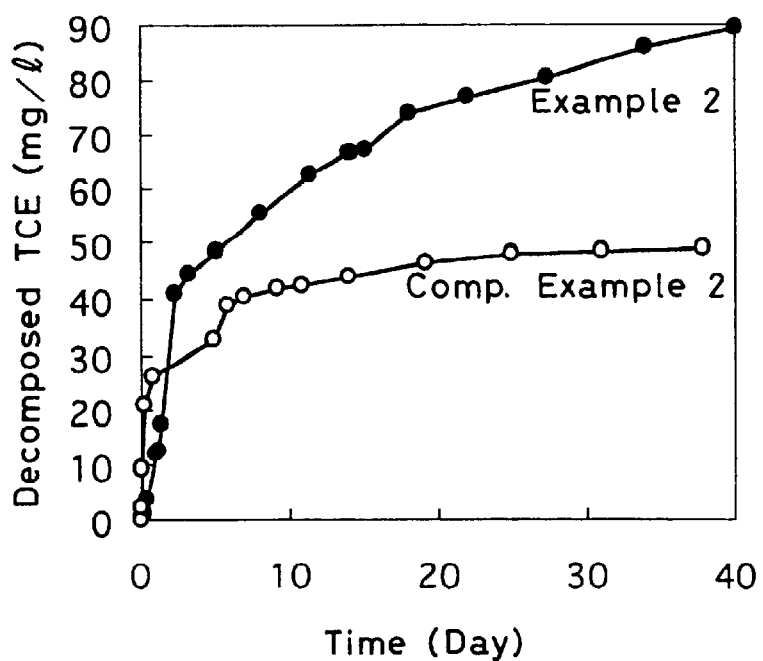
FIG. 5 is a graph showing the results of Example 2 and Comparative Example 2.

The observed temporal change in the amount of consumption of TCE (given as a cumulative amount) by the biodegradation by *Pseudomonas putida* KN1-200A and by *Pseudomonas putida* KN1 (pNIN205), respectively, is shown in the graph of FIG. 5.

As seen from FIG. 5, the amount of consumption of TCE due to the biodegradation by *Pseudomonas putida* KN1 (pNIN205) (Comparative Example 2) became about one half of that by *Pseudomonas putida* KN1-200A (Example 2) after 40 days. From this, it is seen that the TCE-biodegradability of a gene recombinant having an integrated gene sequence containing a promoter, a TCE decomposition-facilitating gene and a TCE decomposing gene in the foreign plasmid per unit cell population is lower than that of a gene recombinant having such a gene sequence integrated in the chromosome.

Example 3

Chlorinated ethylene-biodegradability of a gene recombinant in which a DNA fragment expressing a function for terminating gene transcription is integrated downstream from a recombinant DNA sequence composed of a promoter and a CE decomposing gene group was tested using the cell strains given below.

1. Preparation of *Pseudomonas putida* KN1-210A

A terminator $rrnBT_1T_2$ of 5SrRNA originating from *E. coli* was inserted into the chromosome of *Pseudomonas putida* KN1-200A prepared in Example 1, at its EcoT22I site including the initiation point (ATG) of the gene pheF. The practical procedures were as given below and performed in the same manner as in the case of the tac-promoter by means of a homologous recombination as explained in FIG. 6.

Figure 6:
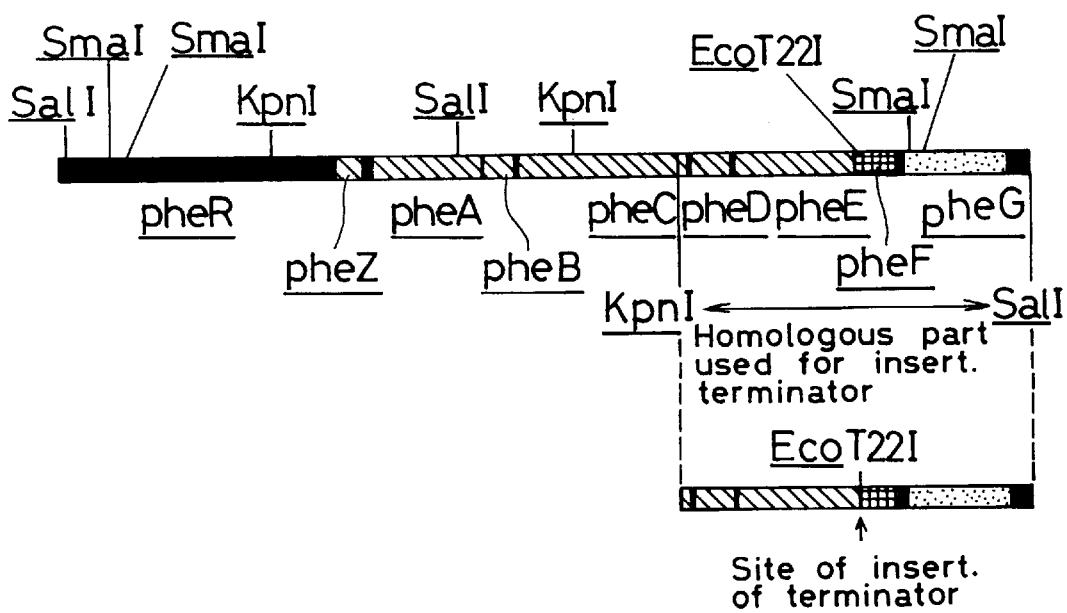
FIG. 6 shows the course of insertion of the homologous part required for inserting the gene group (pheR to pheG) of phenol-hydroxylase and the terminator into pKNA82 in a schematic gene map.
Figure 6:
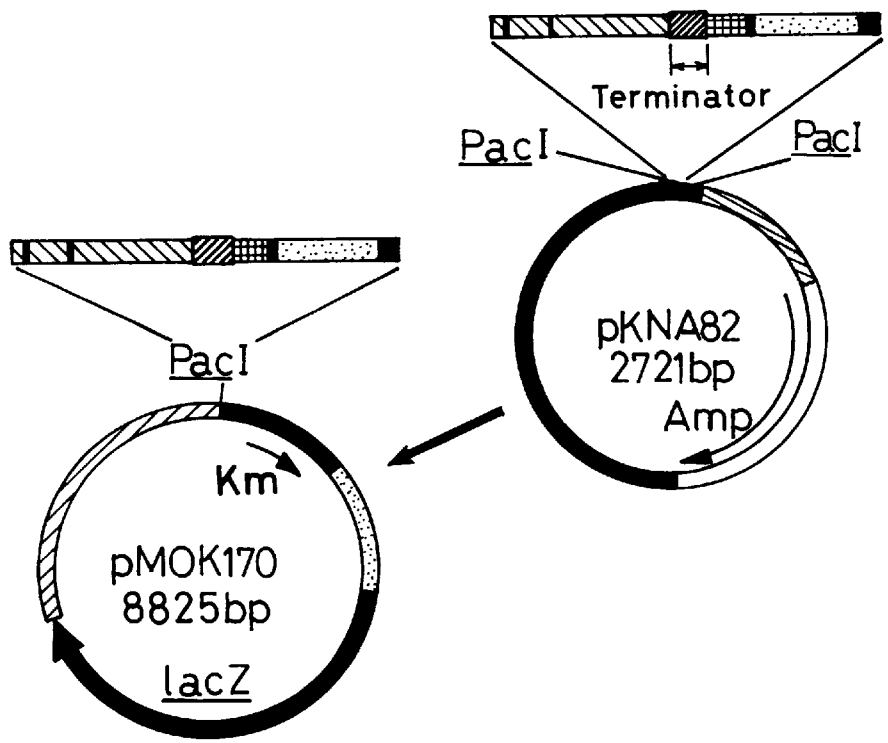

1) The homologous part was the sequence starting from the KpnI site close to pheD among the two KpnI sites in pheC in the PH gene group, as shown in FIG. 6, up to the SalI site downstream from pheG. This homologous part was inserted into pKNA82 in between its KpnI site and SalI site.

2) The resulting pKNA82 having integrated with the KpnI-SalI fragment (about 3.1 kb) was subjected to digestion and de-phosphatization by the EcoT22I present at nearly the center of the inserted fragment, whereupon the terminal ends were flattened by T4 polymerase.

3) Then, a terminator $rrnBT_1T_2$ of 5SrRNA of *E. coli* was synthesized by PCR using the chromosome of *E. coli* HB101 as the template and using the following primer pair:

Upper primer: 5'-GG AAGCTTTAGGGAACTGCCAGGCATC-3' (SEQ ID NO: 7)

Lower primer: 5'-GG GCATGCAAGAGTTTGTAGAAACGC-3' (SEQ ID NO: 8)

(the underlined portion of the upper primer indicates the HindIII site and the underlined portion of the lower primer indicates the SphI site).

4) The terminator $rrnBT_1T_2$ having a length of about 250 bp synthesized in 3) above was subjected to digestion using HindIII and SphI and then to treatment with T4 polymerase to flatten both ends. This was integrated with the vector prepared in 2) above using T4 ligase. Among the so-integrated terminators $rrnBT_1T_2$, one in which the flattened HindIII site is upstream and the flattened SphI site is downstream was selected. By this, it was made possible to effectively terminate the transcription of the gene from the tac-promoter inserted upstream of the PH gene group, by the inserted terminator.

5) The homologous part and the inserted $rrnBT_1T_2$ were excised by the PacI existing on both ends of pKNA82 and were inserted into pMOK170 at its PacI site. The so-obtained plasmid was introduced into cell strain *E. coli* S17-1, which was conjugated with *Pseudomonas putida* KN1-200A, whereby a gene recombinant *Pseudomonas putida* KN1-210A in which the terminator $rrnBT_1T_2$ was integrated in EcoT22I of pheF on the chromosome by the homologous recombination was obtained and separated selectively. These procedures were performed in the same way as in the preparation and selection of the above-described *Pseudomonas putida* KN1-200A.

6) Preparation of pMOK170 (the Vector in which $rrnBT_1T_2$ Terminator was Removed from pMOK180)

The XhoI site in a kanamycin-resistant gene was excised from a PstI site of the multicloning site of pMOK180 and the rrnBT₁T₂ terminator in this vector was excised together with a part of the kanamycin-resistant gene. Into this portion of the excised kanamycin-resistant gene, a corresponding XhoI fragment from the PstI of a kanamycin-resistant gene in pUK4K supplied from the firm Pharmacia was inserted. By this operation, the rrnBT₁T₂ terminator was able to be deleted.

2. Tests for Biodegradation of Chlorinated Ethylene

Figure 7:
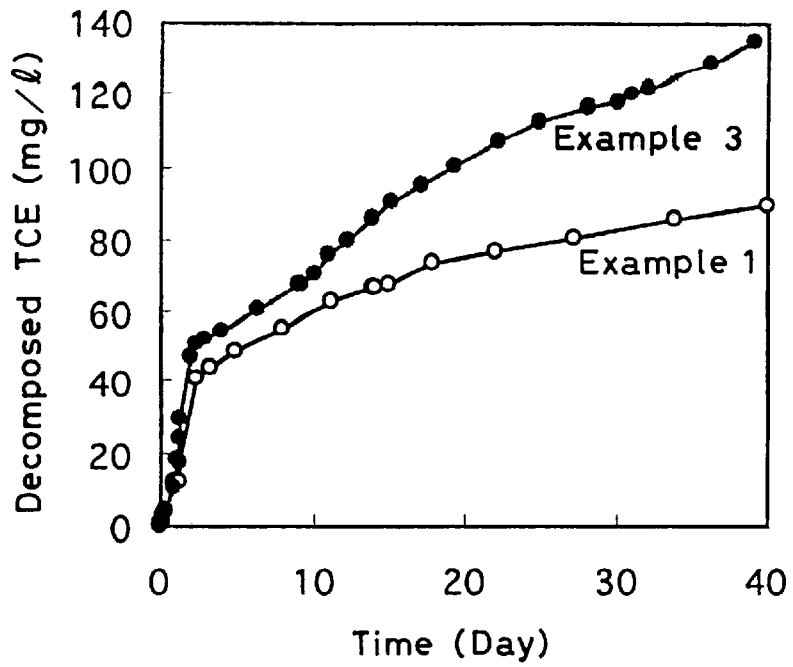
FIG. 7 is a graph showing the results of Example 3 and Comparative Example 1.

Using the gene recombinant obtained as above, tests for the biodegradation of trichloroethylene (TCE) were carried out in the same way as in Example 1. The observed temporal change in the amount of decomposed TCE due to the biodegradation by the gene recombinant of Example 3 is shown in the graph of FIG. 7. Also the test results of Example 1 are plotted on the graph of FIG. 7.

As seen in FIG. 7, the gene recombinant of Example 3 brings about a high biodegradability for TCE all over the entire test period of 40 days which is even higher than that of the gene recombinant of Example 1. Thus, the gene recombinant *Pseudomonas putida* KN1-210A, in which a terminator is inserted into the gene sequence at a lower reach from the PH gene in the chromosome (Example 3), exhibits almost comparable biodegradability to that of the gene recombinant *Pseudomonas putida* KN1-200A (Example 1) for about four days from the start, but the TCE decomposing rate is higher thereafter for the gene recombinant having the integrated terminator. The amount of decomposition of TCE for *Pseudomonas putida* KN1-210A reached about 1.6 times that for *Pseudomonas putida* KN1-200A at the end of the 40 days' test period.

From the above, it is ascertained that a gene recombinant exhibiting a higher biodegradability for chlorinated ethylene can be obtained by inserting into the chromosomal gene sequence, upstream from the CE decomposition-facilitating gene pheZ, a promoter inducing a constitutive expression and downstream from the CE decomposing gene a terminator.

Example 4 and Comparative Example 3

Tests for the biodegradability of a gene recombinant for TCE were carried out using the cell strains given below in which a foreign plasmid having a PH gene and a terminator inserted downstream from the PH gene was introduced.

1) Cell Strains Employed

*Pseudomonas putida* KN1-210A: This is the same as that of Example 3.

*Pseudomonas putida* KN1 (pNIN205): This is the same as that of Comparative Example 2.

2) TCE Biodegradability Tests

The test method was the same as in Example 3.

3) Test Results

Figure 8:
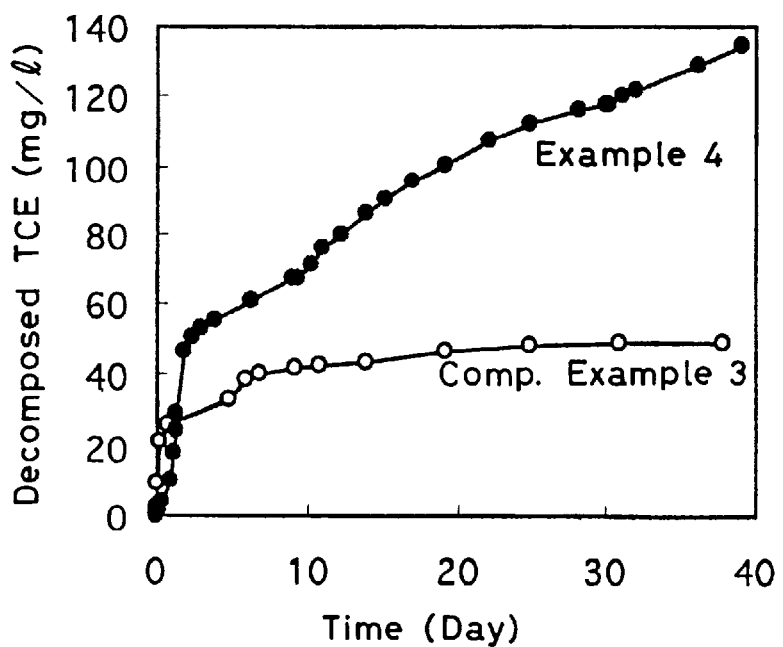
FIG. 8 is a graph showing the results of Example 4 and Comparative Example 3.

The observed temporal change in the amount of decomposition of TCE by the biodegradation by *Pseudomonas putida* KN1 (pNIN205) (Comparative Example 3) and by *Pseudomonas putida* KN1-210A (Example 4), respectively, is shown in the graph of FIG. 8. The amount of decomposition of TCE by *Pseudomonas putida* KN1 (pNIN205) after a 40 days' test period was as low as 40 mg/liter which corresponds to about 3/10 of that by *Pseudomonas putida* KN1-210A. From this, it is seen that insertion of a terminator downstream of the PH gene existing in a foreign plasmid gene does not cause an increase in the biodegradability of the resulting gene recombinant.

What is claimed is:

1. A gene recombinant capable of expressing a biodegradability for chlorinated ethylene, said gene recombinant comprising a recombinant DNA sequence carried on a chromosome, said recombinant DNA sequence comprising:
   a phenol-hydroxylase gene originating from a phenol-metabolizable bacterium capable of bio-degrading chlorinated ethylene, said phenol-hydroxylase gene comprising a gene for facilitating decomposition of chlorinated ethylene and a series of genes for decomposing chlorinated ethylene; and
   a promoter inserted upstream of the gene for facilitating decomposition of chlorinated ethylene by 1–500 base pairs.

2. A gene recombinant capable of expressing a biodegradability for chlorinated ethylene, said gene recombinant comprising a recombinant DNA sequence carried on a chromosome, said recombinant DNA sequence comprising:
   a phenol-hydroxylase gene originating from a phenol-metabolizable bacterium capable of bio-degrading chlorinated ethylene, said phenol-hydroxylase gene comprising a gene for facilitating decomposition of chlorinated ethylene and a series of genes for decomposing chlorinated ethylene; and
   a terminator inserted downstream of the phenol-hydroxylase gene by 1–500 base pairs.

3. A gene recombinant capable of expressing a biodegradability for chlorinated ethylene, said gene recombinant comprising a recombinant DNA sequence carried on a chromosome, said recombinant DNA sequence comprising:
   a phenol-hydroxylase gene originating from a phenol-metabolizable bacterium capable of bio-degrading chlorinated ethylene, said phenol-hydroxylase gene comprising a gene for facilitating decomposition of chlorinated ethylene and a series of genes for decomposing chlorinated ethylene;
   a promoter inserted upstream of the gene for facilitating decomposition of chlorinated ethylene by 1–500 base pairs; and
   a terminator inserted downstream of the phenol-hydroxylase gene by 1–500 base pairs.

4. A gene recombinant capable of expressing a biodegradability for chlorinated ethylene, said gene recombinant comprising a recombinant DNA sequence carried on a chromosome, said recombinant DNA sequence comprising:
   a phenol-hydroxylase gene originating from Pseudomonas putida KWI-9, said phenol-hydroxylase gene comprising a gene for facilitating decomposition of chlorinated ethylene comprising pheZ and a series of genes for decomposing chlorinated ethylene comprising pheA, pheB, pheC, pheD and pheE; and
   a promoter inserted upstream of the gene for facilitating decomposition of chlorinated ethylene by 1–500 base pairs.

5. A gene recombinant capable of expressing a biodegradability for chlorinated ethylene, said gene recombinant comprising a recombinant DNA sequence carried on a chromosome, said recombinant DNA sequence comprising:
   a phenol-hydroxylase gene originating from Pseudomonas putida KWI-9, said phenol-hydroxylase gene comprising a gene for facilitating decomposition of chlorinated ethylene comprising pheZ and a series of genes for decomposing chlorinated ethylene comprising pheA, pheB, pheC, pheD and pheE; and
   a terminator inserted downstream of the phenol-hydroxylase gene by 1–500 base pairs.

6. A gene recombinant capable of expressing a biodegradability for chlorinated ethylene, said gene recombinant comprising a recombinant DNA sequence carried on a chromosome, said recombinant DNA sequence comprising:
   a phenol-hydroxylase gene originating from Pseudomonas putida KWI-9, said phenol-hydroxylase gene comprising a gene for facilitating decomposition of chlorinated ethylene comprising pheZ and a series of genes for decomposing chlorinated ethylene comprising pheA, pheB, pheC, pheD and pheE;
   a promoter inserted upstream of the gene for facilitating decomposition of chlorinated ethylene by 1–500 base pairs; and
   a terminator inserted downstream of the phenol-hydroxylase gene by 1–500 base pairs.

7. The gene recombinant of claim 1, wherein said recombinant DNA sequence comprises SEQ ID NO: 1.

8. The gene recombinant of claim 2, wherein said recombinant DNA sequence comprises SEQ ID NO: 1.

9. The gene recombinant of claim 3, wherein said recombinant DNA sequence comprises SEQ ID NO: 1.

10. The gene recombinant of claim 4, wherein said recombinant DNA sequence comprises SEQ ID NO: 1.

11. The gene recombinant of claim 5, wherein said recombinant DNA sequence comprises SEQ ID NO: 1.

12. The gene recombinant of claim 6, wherein said recombinant DNA sequence comprises SEQ ID NO: 1.

13. A gene recombinant as claimed in claim 1, wherein the phenol-metabolizable bacterium capable of bio-degrading chlorinated ethylene belongs to the genus Pseudomonas.

14. A gene recombinant as claimed in claim 1, wherein the phenol-metabolizable bacterium capable of bio-degrading chlorinated ethylene is *Pseudomonas putida* KWI-9.

15. A gene recombinant as claimed in claim 1, wherein the phenol-metabolizable bacterium capable of bio-degrading chlorinated ethylene is *Pseudomonas putida* KWI-9 and the gene recombinant comprises the recombinant DNA sequence carried on the chromosome of *Pseudomonas putida* KWI-9.

16. A gene recombinant as claimed in claim 1, wherein the phenol-metabolizable bacterium capable of bio-degrading chlorinated ethylene is *Pseudomonas putida* KWI-9 and the phenol-hydroxylase gene comprises a gene for facilitating decomposition of chlorinated ethylene comprising pheZ and a series of genes for decomposing chlorinated ethylene comprising pheA, pheB, pheC, pheD and pheE.

17. A gene recombinant as claimed in claim 1, wherein the phenol-metabolizable bacterium capable of bio-degrading chlorinated ethylene is *Pseudomonas putida* KWI-9, and the phenol-hydroxylase gene comprises a gene facilitating decomposition of chlorinated ethylene comprising pheZ, a series of genes for decomposing chlorinated ethylene comprising pheA, pheB, pheC, pheD and pheE and the gene recombinant comprises the recombinant DNA sequence carried on the chromosome of *Pseudomonas putida* KWI-9.

18. A gene recombinant as claimed in claim 2, wherein the terminator has a stem-and-loop structure.

19. A gene recombinant as claimed in claim 4, wherein the phenol-metabolizable bacterium capable of bio-degrading chlorinated ethylene is *Pseudomonas putida* KWI-9 and the gene recombinant comprises the recombinant DNA sequence carried on the chromosome of *Pseudomonas putida* KWI-9.

20. A method of biological treatment of chlorinated ethylene comprising subjecting chlorinated ethylene to a biological digestion by a gene recombinant as defined in claim 17.

21. A method of biological treatment of chlorinated ethylene comprising subjecting chlorinated ethylene to a biological digestion by a gene recombinant as defined in claim 19.

22. A method of biological treatment of chlorinated ethylene comprising subjecting chlorinated ethylene to a biological digestion by a gene recombinant as defined in claim 19.

* * * * *

UNITED STATES PATENT AND TRADEMARK OFFICE
CERTIFICATE OF CORRECTION

PATENT NO. : 6,093,556　　　　　　　　　　　　　　　　　　　　Page 1 of 1
DATED : July 25, 2000
INVENTOR(S) : Kanji Nakamura et al.

It is certified that error appears in the above-identified patent and that said Letters Patent is hereby corrected as shown below:

<u>Column 28,</u>
Line 16; change "as defined in Claim 17" to -- as defined in Claim 1 --.
Line 20; change "as defined in Claim 19" to -- as defined in Claim 3 --.
Line 24; change "as defined in Claim 19" to -- as defined in Claim 3 --.

Signed and Sealed this

Twenty-fifth Day of September, 2001

Attest:

*Nicholas P. Godici*

NICHOLAS P. GODICI
*Attesting Officer*　　　*Acting Director of the United States Patent and Trademark Office*

UNITED STATES PATENT AND TRADEMARK OFFICE
CERTIFICATE OF CORRECTION

PATENT NO. : 6,093,556
DATED : July 25, 2000
INVENTOR(S) : Kanji Nakamura et al.

It is certified that error appears in the above-identified patent and that said Letters Patent is hereby corrected as shown below:

<u>Column 28,</u>
Line 20, change "as defined in Claim 19" to -- as defined in Claim 2 --.

Signed and Sealed this

Nineteenth Day of March, 2002

Attest:

JAMES E. ROGAN
*Director of the United States Patent and Trademark Office*

*Attesting Officer*

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 4800 base pairs
      (B) TYPE: nucleic acid
      (C) STRANDEDNESS: double
      (D) TOPOLOGY: linear (ii) MOLECULE TYPE: Genomic DNA (vi) ORIGINAL SOURCE:
      (A) ORGANISM: Pseudomonas putida
      (C) INDIVIDUAL ISOLATE: KWI-9

(ix) FEATURE:
      (A) NAME/KEY: peptide
      (B) LOCATION: 127..345
      (C) IDENTIFICATION METHOD: E
      (D) OTHER INFORMATION: pheZ of phenol-hydroxylase (ix) FEATURE:
      (A) NAME/KEY: peptide
      (B) LOCATION: 434..1429
      (C) IDENTIFICATION METHOD: E
      (D) OTHER INFORMATION: pheA of phenol-hydroxylase -continued (ix) FEATURE:
        (A) NAME/KEY: peptide
        (B) LOCATION: 1440..1712
        (C) IDENTIFICATION METHOD: E
        (D) OTHER INFORMATION: pheB of phenol-hydroxylase (ix) FEATURE:
        (A) NAME/KEY: peptide
        (B) LOCATION: 1754..3268
        (C) IDENTIFICATION METHOD: E
        (D) OTHER INFORMATION: pheC of phenol-hydroxylase (ix) FEATURE:
        (A) NAME/KEY: peptide
        (B) LOCATION: 3301..3660
        (C) IDENTIFICATION METHOD: E
        (D) OTHER INFORMATION: pheD of phenol-hydroxylase (ix) FEATURE:
        (A) NAME/KEY: peptide
        (B) LOCATION: 3689..4756
        (C) IDENTIFICATION METHOD: E
        (D) OTHER INFORMATION: pheE of phenol-hydroxylase (xi) SEQUENCE DESCRIPTION: SEQ ID NO: 1:

```
CCATTCCGGG TAAACGCGAA ATCCAGGGCG GCCAGAATCC CGACGCGCCT TGTGGCGCCG      60

TCGTTTGCGC CAGCTGGCAC GCTCTTCGCA ATAGAGGCCA TACCGCCCAT GCGAAGGAGC     120

AGCGCCATGA TCAACCAGTC GGTCCCCTTG TTTGAAGCCT CGCCCCGGTT CGTCCGCGTT     180

GATGGCCGCA CGCCCGAGGG CTTTGTGCAG TTCGCGTTCA GCGTGGCGGA CCCCGAGCTC     240

AATGTCGAGC TGATCATGCC CGAGCCGATG TTCGAGGCCT TCTGCAGCGT CAACCACGTG     300

CGCTTCCTGC CGCCGGAGAT CCCCGCGCCC GATCAGGACG ACTGAGCTCG GCCAGTCCCC     360

ACGCACCGGA CCACGCACCC AACCACGCAC AGAACCACCC ACATAAAAAC AGCAAGACCC     420

AGGAGACCAA GCGATGCAAG TCGATATCAA GACCCAGCAG ATCCAGCCGC TGCGCCAGAC     480

CTACGGCCAT GTGGCGCGCC GCTTTGGCGA CAAGCCCGCC TCGCGCTACC AGGAGGCCAC     540

CTACGACGTG CAGTCGGAAG TGAATTTCCA CTACCGCCCG ACGTGGGACT CGCAACACGA     600

GATCTACGAC AAGCGCCGCA CCGCGATCGT GATGGCGGAC TGGTACGCGC TCAAGGACCC     660

GCGCCAATAC TTCTACGGCG CTTACGTGAC GGCGCGTGGC CGCCAGCAGG ATGCCACCGA     720

GAAGAGCTTC GCCTTCGTGG AAAAGCGCGG CTTGCTGCAG GCGCTGCCTG CCGAATGGCA     780

GGACCGCCTG GCCGACGGCC TGCTGCCGCT GCGCCATGTG GAGTGGGGCG CCAACATGAA     840

CAACTTCTAT TGCGCCGACT ACGGCTGGGG CACGGCCATC ACCCAGGCCT GCACCTACTG     900

CGCGATGGAT CGCCTCGGCA TTGCCCAGTA CCTGTCGCGC ATCGGCATGC TGCTGGATGG     960

CAACACCGGT GTGGCGCTGG AGCGCGCCAA GGTGGCCTGG ATGGAGAGCG CGGCGTGGCA    1020

GCCGATGCGC CGGCTGGTCG AGCGCAGCTT TGTGATCGAG GACTGGTTCG AGACCTTTGT    1080

CACCCAGAAC CTGGTGCTCG ACGGCCTGCT TTACCCGCTG GTGTACCAGC ACGCCGACGC    1140

GGCCATCGTG CGCGCCTGCG GCACCGGGCT GGCGGTGCTG ACCGAGTTCA TGAATGACTG    1200

GCGCGAGGAG CACGCACGCT GGGTCGACGC GGTGATCCAG ACCGCCGCGG CAGAGTCCGA    1260

TGCCAATCGC ATGCTGCTGT CCGGCTGGGC CCGCGCCGCG CGCGCGCAGG TGGCTGAGGC    1320

GCTGGTGCCG GTGGCCGACA CCTTGCTGGG CGAGGGCGGC GAGCAGGTGG TGGCGCTGTG    1380

CGTGGAGCAG TTCGACGTGC GTCTTAACAA GCTTGGCCTT GCCGCCTGAG GAAACCGCCA    1440

TGACCGCCAA TGTGTATATC GCGCTGCAGA GCAACGACGA CACCCGTCCC ATCATCGAGG    1500

CCATCACCGA GGCCAACCCG CACGCGGTGG TGTCGCAGTT TCCCGCCATG GTGAAGATCG    1560

ATGCGCCGGG ACACCTGACC ATCCTGCGCG AACTGGTCTC CGACAAGCTC GGGCGCGACT    1620
```

-continued

| | | | | |
|---|---|---|---|---|
|GGGACCTGCA|GGAGATTCAC|CTGAACCTGA|TTTCGCTGTC|GGGAAACATC|GACGAAGACG|1680|
|ACGACGCCTT|CACCCTGCAC|TGGAACGCCT|GAATCGGCCC|GCCCACCGCA|AAGACAAACG|1740|
|GAGACAAAAC|ACCATGGACG|CACGCAAGAA|GCTGAACCTG|CGGGAAAAAT|ACGCGACGAT|1800|
|GACGCGCGAC|CTCGGCTGGG|AAACCACCTA|CGAGCCGATG|GACAAGGTCT|TTCCCTACGA|1860|
|CAAGTACGAA|GGCATCAAGA|TCCATGACTG|GGACAAATGG|GAAGACCCGT|TTCGCATGAC|1920|
|CATGGACGCC|TACTGAAAAT|ACCAGTCGGA|GAAGGAGCGC|AAGCTGTACG|CGATCATCGA|1980|
|TTCGTTCGTG|CAGAACAATG|GCCACCTCAA|CGTCTCGGAC|CCGCGCTACC|TGAACGCGCT|2040|
|GCGCCTGTTC|CTGACCGGCG|TGACGCCGCT|GGAGTACGCG|GCGCACCGCG|GCTATGCCCA|2100|
|CCTCGGGCGG|CACTTTCGCG|GCGCCGGCGC|GCGGGTGGCG|GCGCAGATGC|AGTCGATCGA|2160|
|CGAGCTGCGC|CACGCCCAGA|CCCAGATGCA|CACGCTGTCG|GTCTACAACA|AGTACTTCAA|2220|
|CGGCTTCGGC|GAATGGCAGC|ACATGCACGA|CCGGGTCTGG|TACCTGTCCG|TGCCCAAGTC|2280|
|CTATTTCGAA|GACGCCATGA|GCGCGGGGCC|GTTCGAGTTC|ATCACCGCGA|TCTCGTTCTC|2340|
|CTTCGAGTAT|GTGCTGACCA|ACCTGCTGTT|CATGCCCTTC|ATGTCGGGTG|CGGCCTACAA|2400|
|CGGCGACATG|GCCACGGTGA|CCTTCGGCTT|CTCGGCACAG|TCCGACGAAT|CGCGCCATAT|2460|
|GACGCTGGGC|CTGGAAGTGG|TGAAGTTCCT|GTGCCAGCAG|GACCCGGACA|ATATCCCCAT|2520|
|CCTGCAGAAG|TGGCTGGACA|AATGGTTCTG|GCGCGGCTTT|CGCCTGCTTA|CGCTGGTCGG|2580|
|CATGATGATG|GACTACATGC|TGCCCAAGCG|CGTGATGTCG|TGGGCGGAAG|CCTGGGAGAT|2640|
|GTACTTCGAG|CAGGCCGGCG|GCGCGCTGTT|CAAGGACCTG|GAGCGCTACG|GCCTGCGCAT|2700|
|GCCCAAGTAC|CACGAGGTGG|CCACCAAGAC|CAAGGACCGC|ATCACCCACG|AGGCCTGGGG|2760|
|CACCTTCTAC|AACTACGCTG|CCGCGGCCGG|CTTCCATACC|TGGGTGCCCA|AGCAGGACGA|2820|
|GATGGCCTGG|CTGACGGAGA|AATATCCCGA|CACCTTCGCG|CGCTACTACA|AGCCGCGCCT|2880|
|CGATTACTGG|CAGGAACGCC|AGCAGCAAGG|CGAGCGCTTC|TACAACGCCA|CGCTGCCGAT|2940|
|GCTGTGCCAG|ACCTGCCAGA|TCCCGATGGT|GTTCTCGGAG|CCGGACGACC|CCACCCAGAC|3000|
|CTGCTACCGG|GAGAGCAGCT|ACCACGGCAT|GCGGTTCCAC|TTCTGCTCGG|ACGGCTGCAA|3060|
|GGACATCTTC|GATGGCGAGC|CGCAGAAGTA|CGCGCAGGCC|TGGTTGCCTG|TGCACCAGAT|3120|
|CTACCAGGGC|AACTGCGGCG|GTGGATCGCT|GGACGACGTG|CTCAAGTGGT|ACCGCATCAA|3180|
|CCCTGGCGCG|GACAACCTGG|ATTTTGAAGG|TTCGCAGGAT|CAGAAGAACT|GGAACGCCTG|3240|
|GAAAGGCGTG|CCGGGCACGG|CTGCCTGAGC|GGCCGGCATA|CAAGAGATAA|GGAGACCACC|3300|
|ATGTCCGTCG|TATCCATTGG|CCCCTACACG|TTCGAGCCCG|CCGATCGGGA|GGCCGTGTTC|3360|
|CACGGCAACC|GCCTGCTCTA|TATCGGCTGG|GACCGCCACC|TGCTGTTTTG|TGCGCCGCAT|3420|
|TGCCTTCCCT|TGCCGCCGTC|GATGCGCCTG|CGCGATGTCG|TGGAGAACGT|GCTGCCGGGC|3480|
|GTCTACGGCT|ATCACCCCGA|CTTTGCCCGC|ATCGACTGGA|GCCGCGTGGA|GTGGCTGCGC|3540|
|GGCGGCGAGC|CCTGGCAGCC|AGACCTTGAC|CGCACGCTGG|AAGAGAACGG|CCTGGGCCAC|3600|
|AAGGCGGTGA|TCCGGTTACG|CACACCGGGG|CTGGATGGCA|TTGGCGGCAG|TGGCAGCTAA|3660|
|CAGTGGCAGC|TAAGGTAGGA|GACACAAGAT|GTATTCCCTG|ACCATTGAAC|CGATCGGGCA|3720|
|GACCATCCCC|ATCGCGCCGG|GCCAGACCGT|GCTGGATGCC|TGCCTGCGCA|ACGGCGTGTG|3780|
|GCTGCCGCAC|GCCTGCTGCC|ACGGGCTGTG|CGCCACCTGC|AAGGTGCAGG|TGGTGGAGGG|3840|
|CGAATTCGAG|CATGGAGAGG|CCTCCAGCTT|CGCGCTGATG|GACTTCGAGC|GCGACAGCGG|3900|
|GCAGTGCCTG|GCTTGCTGCG|CCACCGCGCA|GTCCGACATG|GTGATCGAGG|CCGATATCGA|3960|

```
GGAAGACGCC GACTCGCTCG GCCTGCCGCT GGCTGACTAT CGTGCCGAGG TGGTGGAGGC    4020

CCGCGCGCTG ACCCCCACCA TCCGCGGCAT CTGGCTGCGC GTGAAGGGGG CGCCGCGGC     4080

TGCCTTCCAG GCCGGCCAGT ACCTCAACCT GCGCGTGCCG GGCTGCGACC AGCCGCGTGC    4140

GTTCTCGCTG GCCAACCGTC CCGGCGATGA CCTGGTGGAG CTGCATGTGC GGCGGGTGGA    4200

AGGCGGGCAG GCTACCGGCT ACCTGCACGA TCAGCTGTCG GTGGGTGACG AACTCGGGTT    4260

TTCCGCGCCT TACGGCCGCT TCTTCGTGCG CAAGTCAGCG CAAAAGCCGA TGCTGTTCCT    4320

GGCGGGCGGC TCGGGCTTGT CCAGCCCGCG CGCCATGATC CTGGACATGC TGGCTGCCGG    4380

CGAGACCCTG CCGATCACGC TGGTGCAAGG CGCGCGCAAC CGCACGGAGC TGTACTACGA    4440

CGAGGCGTTC CGTGCACTGG CCGGCGCGCA CCCCAACTTC CGCTATGTGC CCGCGCTCTC    4500

CGACGAACCG GCGGACAGCG GCTGGGACGG CGCGCGCGGC TATGTGCATG ACGTCCTGCA    4560

CGGCCTTTAC GCCAATGGCG CGACCGCCGA CTTCCGTGGC CACAAGGCCT ATCTGTGCGG    4620

CCCGCCGCCG ATGATCGAAG CCTGCATCCG CACGTTGATG CAGGGCCGGC TGTTCGAGGA    4680

GGACATCCAC ACCGAGAAAT TCATCTCGGC CGGCGACGCA CAGAACAGCG CGCGCAGCCC    4740

GCTGTTCAAG ATCTGATGGA GGGCGCGGCA TGCATACCGT CGAGATCGCG GGCAGCGGCC    4800
```

(2) INFORMATION FOR SEQ ID NO: 2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other nucleic acid (synthetic primer)

(ix) FEATURE:
        (B) LOCATION: 4..9
        (C) IDENTIFICATION METHOD: S
        (D) OTHER INFORMATION: EcoRI site (xi) SEQUENCE DESCRIPTION: SEQ ID NO: 2:

```
GGGGAATTCG GGGAGGGGG TAAGGGGGTG GTG                                    33
```

(2) INFORMATION FOR SEQ ID NO: 3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other nucleic acid (synthetic primer)

(ix) FEATURE:
        (B) LOCATION: 4..9
        (C) IDENTIFICATION METHOD: S
        (D) OTHER INFORMATION: SmaI site (xi) SEQUENCE DESCRIPTION: SEQ ID NO: 3:

```
GGGCCCGGGA AGAGCGTGCC AGCTGGCGCA AAC                                   33
```

(2) INFORMATION FOR SEQ ID NO: 4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other nucleic acid (synthetic primer)

(ix) FEATURE:
        (B) LOCATION: 4..9
        (C) IDENTIFICATION METHOD: S
        (D) OTHER INFORMATION: BamHI site (xi) SEQUENCE DESCRIPTION: SEQ ID NO: 4:

GGGGGATCCC GCAATAGAGG CCATACCGCC CA                                    32

(2) INFORMATION FOR SEQ ID NO: 5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other nucleic acid (synthetic primer)

(ix) FEATURE:
        (B) LOCATION: 4..9
        (C) IDENTIFICATION METHOD: S
        (D) OTHER INFORMATION: BamHI site (xi) SEQUENCE DESCRIPTION: SEQ ID NO: 5:

CGCGGATCCG GCGGTTTCCT CAGGCGGCAA GGC                                   33

(2) INFORMATION FOR SEQ ID NO: 6:

(i) SEQUENCE CHARACTERISTICS:
        (A) LENGTH: 97 base pairs
        (B) TYPE: nucleic acid
        (C) STRANDEDNESS: double
        (D) TOPOLOGY: linear (ii) MOLECULE TYPE: Other nucleic acid (synthetic primer)

(ix) FEATURE:
        (B) LOCATION: 1..6
        (C) IDENTIFICATION METHOD: S
        (D) OTHER INFORMATION: HindIII site (ix) FEATURE:
        (A) NAME/KEY: promoter
        (B) LOCATION: 7..91
        (C) IDENTIFICATION METHOD: S (ix) FEATURE:
        (B) LOCATION: 92..97
        (C) IDENTIFICATION METHOD: S
        (D) OTHER INFORMATION: BamHI site (xi) SEQUENCE DESCRIPTION: SEQ ID NO: 6:

AAGCTTACTC CCCATCCCCC TGTTGACAAT TAATCATCGG CTCGTATAAT GTGTGGAATT     60

GTGAGCGGAT AACAATTTCA CACAGGAAAC AGGATCC                             97

(2) INFORMATION FOR SEQ ID NO: 7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other nucleic acid (synthetic primer)

(ix) FEATURE:
        (B) LOCATION: 3..8
        (C) IDENTIFICATION METHOD: S
        (D) OTHER INFORMATION: HindIII site (xi) SEQUENCE DESCRIPTION: SEQ ID NO: 7:

```
GGAAGCTTTA GGGAACTGCC AGGCATC                                              27

(2) INFORMATION FOR SEQ ID NO: 8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid (synthetic primer)

(ix) FEATURE:
        (B) LOCATION: 3..8
        (C) IDENTIFICATION METHOD: S
        (D) OTHER INFORMATION: SphI site (xi) SEQUENCE DESCRIPTION: SEQ ID NO: 8:

GGGCATGCAA GAGTTTGTAG AAACGC                                               26
```